United States Patent
Huang

(10) Patent No.: US 12,415,846 B2
(45) Date of Patent: Sep. 16, 2025

(54) RECOMBINANT HUMAN 2IG-B7-H3 PROTEIN CODING GENE, RECOMBINANT VECTOR, HOST CELL COMPRISING THE SAME, PHARMACEUTICAL COMPOSITION AND USE THEREOF

(71) Applicants: Haidong Huang, Beijing (CN); Xiaoyi Zhou, Zhejiang (CN); Hanqiang Chen, Zhejiang (CN)

(72) Inventor: Haidong Huang, Beijing (CN)

(73) Assignee: Shanghai Renyousheng Gene Technology Co., Ltd., Shanghai (CN)

( * ) Notice: Subject to any disclaimer, the term of this patent is extended or adjusted under 35 U.S.C. 154(b) by 837 days.

(21) Appl. No.: 17/417,991

(22) PCT Filed: Dec. 24, 2018

(86) PCT No.: PCT/CN2018/123049
§ 371 (c)(1),
(2) Date: Jun. 24, 2021

(87) PCT Pub. No.: WO2020/132789
PCT Pub. Date: Jul. 2, 2020

(65) Prior Publication Data
US 2022/0073587 A1 Mar. 10, 2022

(51) Int. Cl.
C07K 14/705 (2006.01)
A61K 38/00 (2006.01)
A61P 35/00 (2006.01)
C12N 15/86 (2006.01)

(52) U.S. Cl.
CPC ........ *C07K 14/70532* (2013.01); *A61P 35/00* (2018.01); *C12N 15/86* (2013.01); *A61K 38/00* (2013.01); *C07K 2319/30* (2013.01)

(58) Field of Classification Search
CPC .... C07K 14/70532; A61P 35/00; C12N 15/86
See application file for complete search history.

(56) References Cited

U.S. PATENT DOCUMENTS

| | | | |
|---|---|---|---|
| 2003/0134283 A1 | 7/2003 | Peterson et al. | |
| 2005/0002935 A1* | 1/2005 | Ling ................ | A61P 37/00 514/14.1 |
| 2006/0154313 A1 | 7/2006 | Anderson et al. | |
| 2007/0099251 A1* | 5/2007 | Zhang ............... | G01N 33/6848 435/7.92 |
| 2013/0149236 A1 | 6/2013 | Johnson et al. | |
| 2013/0259923 A1 | 10/2013 | Bancel et al. | |
| 2013/0259924 A1 | 10/2013 | Bancel et al. | |
| 2018/0256644 A1 | 9/2018 | Swanson et al. | |

FOREIGN PATENT DOCUMENTS

| | | | | |
|---|---|---|---|---|
| CN | 1809370 | A | 7/2006 | |
| CN | 103571838 | A | 7/2012 | |
| CN | 106279416 | A | 1/2017 | |
| CN | 109097366 | A | 6/2017 | |
| CN | 108513576 | A | 9/2018 | |
| EA | 201890729 | A1 | 9/2018 | |
| EP | 2295588 | A1 | 3/2011 | |
| JP | 2006523711 | A | 10/2006 | |
| JP | 2015516143 | A | 6/2015 | |
| JP | 2017035086 | A | 2/2017 | |
| JP | 2017121241 | A | 7/2017 | |
| WO | 0210187 | A1 | 2/2002 | |
| WO | 2007047796 | A2 | 4/2007 | |
| WO | 2011109400 | A2 | 9/2011 | |
| WO | WO-2016103269 | A1 * | 6/2016 | ........... C12N 5/0618 |
| WO | 2017222593 | A1 | 12/2017 | |
| WO | 2018017708 | A1 | 1/2018 | |

OTHER PUBLICATIONS

Nat Immunol. Mar. 2001;2(3):269-74 (Year: 2001).*
Tissue Antigens. Aug. 2007;70(2):96-104 (Year: 2007).*
Chapoval et al. (Nat Immunol. Mar. 2001;2(3):269-74; referenced in the IDS submitted Dec. 29, 2021) (Year: 2001).*
Zhou et al. (Tissue Antigens. Aug. 2007;70(2):96-104.; referenced in IDS submitted Sep. 1, 2022) (Year: 2007).*
Foreign Communication from Related Application—Japanese Office Action with English Translation, Japanese Patent Application No. 2021-560752 dated Jun. 14, 2022, 8 pages.
Foreign Communication from Related Application—Russian Office Action with English Translation, Russian Patent Application No. 2021121206/10(044411) dated Jul. 6, 2022, 18 pages.
Foreign Communication from Related Application—Extended European Search Report, European Application No. 18944354.2-1118/ 3889263 PCT/CN2018123049, dated Jul. 19, 2022, 16 pages.
Sambrook, J. et al., "Molecular Cloning, A Laboratory Manual," Cold Spring Harbor Laboratory Press, 1989, 14 pages.
Zhou, Y.H. et al., "4IgB7-H3 is the major isoform expressed on immunocytes as well as malignant cells," Tissue Antigens, 2007, pp. 96-104, vol. 70, Soochow University.
Wang, Ling et al., "B7-H3-mediated tumor immunology: Friend or foe?," International Journal of Cancer, 2014, pp. 2764-2771, vol. 134, No. 12, UICC.
Sun, Jing et al., "Origination of New Immunological Functions in the Costimulatory Molecule B7-H3 the Role of Exon Duplication in Evolution of the Immune System," PLoS ONE, Sep. 13, 2011, 12 pages vol. 6, No. 9.
Shi, Jian et al., "Preparation and application of a novel monoclonal antibody specific for human B7-H3," Molecular Medicine Reports, vol. 14, pp. 943-948, 2016.

(Continued)

Primary Examiner — Fereydoun G Sajjadi
Assistant Examiner — Joel D Levin
(74) Attorney, Agent, or Firm — Conley Rose, P.C.; Rodney B. Carroll

(57) ABSTRACT

The present disclosure relates to the field of genetic engineering, in particular to a recombinant human 2Ig-B7-H3 protein encoding gene, a protein, a recombinant vector, and a pharmaceutical composition including the gene or protein. The recombinant human 2Ig-B7-H3 protein encoding gene comprises a nucleotide sequence shown in SEQ ID NO:1.

13 Claims, 2 Drawing Sheets

Specification includes a Sequence Listing.

(56) References Cited

OTHER PUBLICATIONS

Foreign Communication from Related Application—Second Russian Office Action, Application No. RU 2021121206/10 (044411), dated Aug. 31, 2022, with English translation, 10 pages.
Chapoval, Andrei I. et al., "B7-H3:A costimulatory molecule for T cell activation and IFN-γ production," Nature Immunology, Mar. 2001, vol. 2, No. 3, pp. 269-274, Nature Publishing Group.
Sun, Yuping et al., "B7-H3 and B7-H4 expression in non-small-cell lung cancer," Lung Cancer, 2006, 9 pages, Elsevier Ireland Ltd.
Zhao, Long et al., "Early Detection of Hepatocellular Carcinoma in Patients with Hepatocirrhosis by Soluble B7-H3," Journal of Gastrointestinal Surgery, 2017 vol. 21, pp. 807-812, Springer.
Suh, Woong-Kyung et al., "The B7 family member B7-H3 preferentially down-regulates T helper type 1-mediated immune responses," Nature Immunology, Sep. 2003, vol. 4, No. 9, pp. 899-906, Nature Publishing Group.
"*Homo sapiens* CD276 molecule (CD276), transcript variant 2, mRNA," NCBI Reference Sequence: NM_025240.2, 5 pages, The National Center for Biotechnology Information.
Foreign Communication from Related Application—International Preliminary Report on Patentability and Written Opinion of the International Searching Authority, International Application No. PCT/CN2018/123049, dated Jul. 8, 2021, 6 pages.
Foreign Communication from Related Application—First Office Action from the State Intellectual Property Office of the People's Republic of China, Chinese Application No. 2017104679941, dated Jan. 26, 2021, 7 pages.
Wang, Ling et al., "Expression of costimulatory molecule B7-H3 in human osteosarcoma and its clinical significance," China Oncology, 2015, vol. 25, No. 10, pp. 768-773.

* cited by examiner

SEQUENCE LISTING

```
<160> NUMBER OF SEQ ID NOS: 2

<210> SEQ ID NO 1
<211> LENGTH: 2765
<212> TYPE: DNA
<213> ORGANISM: Artificial Sequence
<220> FEATURE:
<223> OTHER INFORMATION: chemical synthesized DNA

<400> SEQUENCE: 1
ccggcctcag ggacgcaccg gagccgcctt tccgggcctc aggcggattc tccggcgcgg      60
cccgccccgc ccctcggact ccccgggccg ccccggccc ccattcgggc cgggcctcgc     120
tgcggcggcg actgagccag gctgggccgc gtccctgagt cccagagtcg gcgcggcgcg     180 gcagggggcag ccttccacca cggggagccc agctgtcagc cgcctcacag gaagatgctg     240
```

-continued

```
cgtcggcggg gcagccctgg catgggtgtg catgtgggtg cagccctggg agcactgtgg      300
ttctgcctca caggagccct ggaggtccag gtccctgaag acccagtggt ggcactggtg      360
ggcaccgatg ccaccctgtg ctgctccttc tcccctgagc ctggcttcag cctggcacag      420
ctcaacctca tctggcagct gacagatacc aaacagctgg tgcacagctt tgctgagggc      480
caggaccagg gcagcgccta tgccaaccgc acggccctct tcccggacct gctggcacag      540
ggcaacgcat ccctgaggct gcagcgcgtg cgtgtggcgg acgagggcag cttcacctgc      600
ttcgtgagca tccgggattt cggcagcgct gccgtcagcc tgcaggtggc cgctccctac      660
tcgaagccca gcatgaccct ggagcccaac aaggacctgc ggccagggga cacggtgacc      720
atcacgtgct ccagctaccg gggctaccct gaggctgagg tgttctggca ggatgggcag      780
ggtgtgcccc tgactggcaa cgtgaccacg tcgcagatgg ccaacagcag gggcttgttt      840
gatgtgcaca gcgtcctgcg ggtggtgctg ggtgcgaatg gcacctacag ctgcctggtg      900
cgcaaccccg tgctgcagca ggatgcgcac ggctctgtca ccatcacagg gcagcctatg      960
acattccccc cagaggccct gtgggtgacc gtggggctgt ctgtctgtct cattgcactg     1020
ctggtggccc tggctttcgt gtgctggaga aagatcaaac agagctgtga ggaggagaat     1080
gcaggagctg aggaccagga tggggaggga aaggctccaa agcagccct gcagcctctg      1140 aaacactctg acagcaaaga agatgatgga caagaaatag cctgaccatg aggaccaggg     1200
agctgctacc cctccctaca gctcctaccc tctggctgca atgggctgc actgtgagcc      1260 ctgcccccaa cagatgcatc ctgctctgac aggtgggctc cttctccaaa ggatgcgata     1320
cacagaccac tgtgcagcct tatttctcca atggacatga ttcccaagtc atcctgctgc     1380
ctttttcctt atagacacaa tgaacagacc acccacaacc ttagttctct aagtcatcct     1440
gcctgctgcc ttatttcaca gtacatacat ttcttaggga cacagtatac tgaccacatc     1500
accaccctct tcttccagtg ctgcgtggac catctggctg cctttttct ccaaaagatg      1560 caatattcag actgactgac cccctgcctt atttcaccaa agacacgatg catagtcacc     1620
ccggccttgt ttctccaatg gccgtgatac actagtgatc atgttcagcc ctgcttccac     1680
ctgcatagaa tcttttcttc tcagacaggg acagtgcggc ctcaacatct cctggagtct     1740
agaagctgtt tccttttccc tccttcctcc tcttgctcta gccttaatac tggccttttc     1800 cctcccctgcc ccaagtgaag acagggcact ctgcgcccac cacatgcaca gctgtgcatg     1860
gagacctgca ggtgcacgtg ctggaacacg tgtggttccc cctggcccca gcctcctctg    1920 cagtgccccct ctcccctgcc catcctcccc acggaagcat gtgctggtca cactggttct     1980
ccaggggtct gtgatggggc ccctgggggt cagcttctgt ccctctgcct tctcacctct     2040
ttgttccttt cttttcatgt atccattcag ttgatgttta ttgagcaact acagatgtca     2100
gcactgtgtt aggtgctggg ggccctgcgt gggaagataa agttcctccc tcaaggactc     2160
cccatccagc tgggagacag acaactaact acactgcacc ctgcggtttg caggggggctc    2220 ctgcctggct ccctgctcca cacctcctct gtggctcaag gcttcctgga tacctcaccc     2280
ccatcccacc cataattctt acccagagca tgggggttggg gcggaaacct ggagagaggg    2340
acatagcccc tcgccacggc tagagaatct ggtggtgtcc aaaatgtctg tccaggtgtg     2400
ggcaggtggg caggcaccaa ggccctctgg acctttcata gcagcagaaa aggcagagcc     2460
tggggcaggg caggggccagg aatgctttgg ggacaccgag gggactgccc ccacccccca    2520
ccatggtgct attctggggc tggggcagtc ttttcctggc ttgcctctgg ccagctcctg     2580
gcctctggta gagtgagact tcagacgttc tgatgccttc cggatgtcat ctctcccctgc    2640
```

```
cccaggaatg aagatgtga ggacttctaa tttaaatgtg ggactcggag ggattttgta    2700 aactggggt atattttggg gaaataaat gtctttgtaa aaagcttaaa aaaaaaaaa      2760 aaaaa                                                               2765
```

<210> SEQ ID NO 2
<211> LENGTH: 2765
<212> TYPE: DNA
<213> ORGANISM: Artificial Sequence
<220> FEATURE:
<223> OTHER INFORMATION: Wild-type 2Ig-B7-H3 protein encoding gene

<400> SEQUENCE: 2

```
ccggcctcag ggacgcaccg gagccgcctt ccgggcctc aggcggattc tccggcgcgg      60
cccgccccgc ccctcggact ccccgggccg ccccggccc ccattcgggc cgggcctcgc     120
tgcggcggcg actgagccag gctgggccgc gtccctgagt cccagagtcg gcgcggcgcg    180
gcaggggcag ccttccacca cggggagccc agctgtcagc cgcctcacag gaagatgctg    240
cgtcggcggg gcagccctgg catgggtgtg catgtgggtg cagccctggg agcactgtgg    300
ttctgcctca caggagccct ggaggtccag gtccctgaag acccagtggt ggcactggtg    360
ggcaccgatg ccaccctgtg ctgctccttc tcccctgagc ctggcttcag cctggcacag    420
ctcaacctca tctggcagct gacagatacc aaacagctgg tgcacagctt tgctgagggc    480
caggaccagg gcagcgccta tgccaaccgc acggccctct cccggacct gctggcacag     540 ggcaacgcat ccctgaggct gcagcgcgtg cgtgtggcgg acgagggcag cttcacctgc    600
ttcgtgagca tccgggattt cggcagcgct gccgtcagcc tgcaggtggc cgctccctac    660
tcgaagccca gcatgaccct ggagcccaac aaggacctgc ggccagggga cacggtgacc    720
atcacgtgct ccagctaccg gggctaccct gaggctgagg tgttctggca ggatgggcag    780
ggtgtgcccc tgactggcaa cgtgaccacg tcgcagatgg ccaacgagca gggcttgttt    840
gatgtgcaca gcgtcctgcg ggtggtgctg ggtgcgaatg gcacctacag ctgcctggtg    900
cgcaaccccg tgctgcagca ggatgcgcac ggctctgtca ccatcacagg gcagcctatg    960
acattccccc cagaggccct gtgggtgacc gtggggctgt ctgtctgtct cattgcactg    1020
ctggtggccc tggctttcgt gtgctggaga aagatcaaac agagctgtga ggaggagaat    1080
gcaggagctg aggaccagga tggggaggga gaaggctcca gacagccct gcagcctctg    1140 aaacactctg acagcaaga agatgatgga caagaaatag cctgaccatg aggaccaggg    1200
agctgctacc cctccctaca gctcctaccc tctggctgca atggggctgc actgtgagcc    1260 ctgccccaa cagatgcatc ctgctctgac aggtgggctc cttctccaaa ggatgcgata    1320
cacagaccac tgtgcagcct tatttctcca atggacatga ttcccaagtc atcctgctgc    1380
cttttttctt atagacacaa tgaacagacc acccacaacc ttagttctct aagtcatcct    1440
gcctgctgcc ttatttcaca gtacatacat ttcttaggga cacagtacac tgaccacatc    1500
accaccctct tcttccagtg ctgcgtggac catctggctg cctttttct ccaaaagatg     1560 caatattcag actgactgac ccctgcctt atttcaccaa agacacgatg catagtcacc    1620 ccggcctttgt ttctccaatg gccgtgatac actagtgatc atgttcagcc ctgcttccac    1680
ctgcatagaa tcttttcttc tcagacaggg acagtgcggc ctcaacatct cctggagtct    1740
agaagctgtt tccttttcccc tccttcctcc tcttgctcta gccttaatac tggccttttc    1800
cctccctgcc ccaagtgaag acagggcact ctgcgcccac cacatgcaca gctgtgcatg    1860
```

```
gagacctgca ggtgcacgtg ctggaacacg tgtggttccc ccctggccca gcctcctctg  1920
cagtgcccct ctcccctgcc catcctcccc acggaagcat gtgctggtca cactggttct  1980
ccaggggtct gtgatggggc ccctgggggt cagcttctgt ccctctgcct tctcacctct  2040
ttgttccttt cttttcatgt atccattcag ttgatgttta ttgagcaact acagatgtca  2100
gcactgtgtt aggtgctggg ggccctgcgt gggaagataa agttcctccc tcaaggactc  2160
cccatccagc tgggagacag acaactaact acactgcacc ctgcggtttg caggggctc   2220 ctgcctggct ccctgctcca cacctcctct gtggctcaag gcttcctgga tacctcaccc  2280
ccatcccacc cataattctt acccagagca tggggttggg gcggaaacct ggagagaggg  2340
acatagcccc tcgccacggc tagagaatct ggtggtgtcc aaaatgtctg tccaggtgtg  2400
ggcaggtggg caggcaccaa ggccctctgg acctttcata gcagcagaaa aggcagagcc  2460
tggggcaggg cagggccagg aatgctttgg ggacaccgag gggactgccc cccacccccca 2520 ccatggtgct attctggggc tggggcagtc ttttcctggc ttgcctctgg ccagctcctg  2580
gcctctggta gagtgagact tcagacgttc tgatgccttc cggatgtcat ctctccctgc  2640
cccaggaatg aagatgtga  ggacttctaa tttaaatgtg ggactcggag ggattttgta  2700
aactgggggt atattttggg gaaataaaat gtctttgtaa aaagcttaaa aaaaaaaaaa  2760
aaaaa                                                              2765
```

RECOMBINANT HUMAN 2IG-B7-H3 PROTEIN CODING GENE, RECOMBINANT VECTOR, HOST CELL COMPRISING THE SAME, PHARMACEUTICAL COMPOSITION AND USE THEREOF

CROSS-REFERENCE TO RELATED APPLICATIONS

This Application is a filing under 35 U.S.C. 371 of International Application No. PCT/CN2018/123049 filed Dec. 24, 2018, entitled "Mutated Human 2IG-B7-H3 Protein Coding Gene, Recombinant Vector, Host Cell Containing Same, Pharmaceutical Composition and Application thereof," which is hereby incorporated by reference in its entirety.

TECHNICAL FIELD

The present invention relates to the field of genetic engineering, in particular to a human 2Ig-B7-H3 protein encoding gene, a protein encoded thereby, a recombinant vector, a host cell comprising the same, a pharmaceutical composition and use thereof.

REFERENCE TO SEQUENCE LISTING

The instant application contains a Sequence Listing which has been submitted electronically in .txt file format and is hereby incorporated by reference in its entirety. Said .txt file, created on Dec. 12, 2024, is named "4814-00100 Replacement Sequence Listing.txt" and is 7.65 kilobytes in size.

BACKGROUND

The activation of T cells requires two different signals. The first signal comes from the interaction between TCR and the antigen peptide-MHC complex, and the second signal comes from the co-stimulatory signal generated by the combination of the B7 family molecule on the APC and its ligand CD28 family molecule on the T cell, e.g., B7-1B7-2 combined with CD28 and CTLA-4. This pathway is called the classic B7 pathway.

The human B7-H3 gene was first discovered by Chapoval et al. in the cDNA library of human dendritic cells. Since its structure is similar to the gene of the B7 family, it was named B7 Homolog 3, or abbreviated as B7-H3. It is a type I transmembrane glycoprotein, belongs to the immunoglobulin superfamily, and has 20% to 27% sequence homology with other members of the B7 family in the amino acid sequence outside the cell.

B7-H3 has a wide range of expression: B7-H3 is expressed in most tissues in terms of the transcription level, and only in a few tissues (e.g., liver, lung, bladder, testis, prostate, breast, placenta and lymphoid organs, etc in human) in terms of the protein level, and the difference in the expressions of B7-H3 in terms of the gene (mRNA) level and the protein level may be related to the post-transcriptional regulation of the molecule.

In addition to regulating the proliferation of lymphocytes during antigen-specific humoral immunity, B7-H3 is an immune regulatory molecule. In recent years, it has also been found to have important clinical significance in many tumor cells: that is, it may be a regulator of tumor resistance.

The human B7-H3 gene is located on chromosome 15, and the protein has two different forms of spliceosome in the body: 2IgB7-H3 and 4IgB7-H3. The extracellular segment of 2IgB7-H3 is composed of two immunoglobulin domains of IgV-IgC. The applicant hopes to discover the correlation between 2IgB7-H3 gene mutation and tumor resistance through research.

SUMMARY

A technical problem to be solved by the present disclosure is to provide a human 2Ig-B7-H3 protein encoding gene, a protein encoded thereby, a recombinant vector, a host cell comprising the same, a pharmaceutical composition and a use thereof. The human 2Ig-B7-H3 protein coding gene provides a new way to treat cancer.

The present disclosure provides a recombinant human 2Ig-B7-H3 protein coding gene, and the gene has the nucleotide sequence as shown in SEQ ID NO: 1.

The present disclosure provides a human 2Ig-B7-H3 protein, the coding gene of the human 2Ig-B7-H3 protein is the recombinant human 2Ig-B7-H3 protein coding gene.

The present disclosure provides a recombinant vector, including a vector and a target gene carried by the vector, in which the target gene is the recombinant human 2Ig-B7-H3 protein coding gene as described in the above technical solutions.

Preferably, the vector is selected from a group consisting of a cloning vector, an eukaryotic expression vector, a prokaryotic expression vector and a shuttle vector.

The present disclosure provides a pharmaceutical composition, including excipients and one or more of the human 2Ig-B7-H3 protein and the recombinant carrier selected in the above technical solutions.

Preferably, the pharmaceutical composition is an injection, including a pharmaceutically acceptable excipient and one or more selected from the recombinant carriers described in the above technical solutions.

The present disclosure provides a use of the recombinant human 2Ig-B7-H3 protein coding gene described in the above technical solutions in the preparation of a medicament for preventing and treating cancer.

As compared with the prior art, the present disclosure provides a recombinant human 2Ig-B7-H3 protein encoding gene, a protein encoded thereby, a recombinant vector, and a pharmaceutical composition including the gene or protein. The regulatory expression, interaction and signal transmission of the protein encoded by the gene of the present disclosure play an extremely important role in the tumor immune response process, and especially provide a new and beneficial way for the prevention and treatment of cancer.

DETAILED DESCRIPTION

Figure 1:
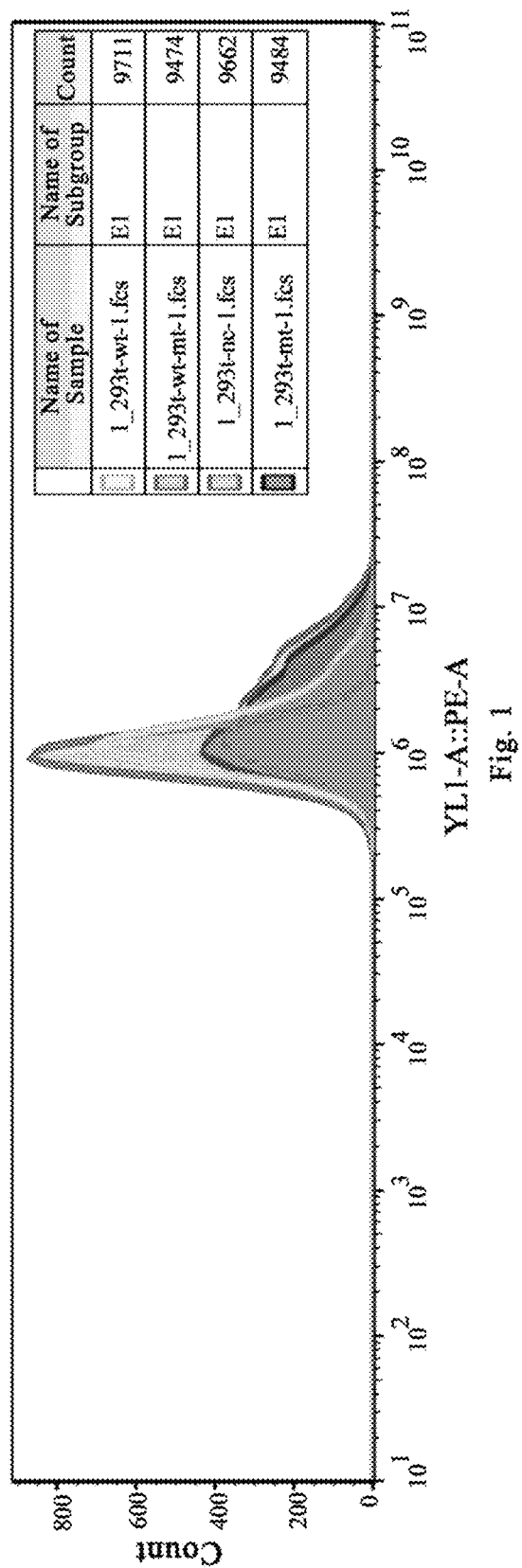
FIG. 1 shows the results of flow cytometric data analysis of 293T cells.

Hereinafter, exemplary embodiments of the present disclosure will be described in more detail in conjunction with the drawings. Although the drawings show exemplary embodiments of the present disclosure, it should be understood that the present disclosure can be implemented in various forms and should not be limited by the embodiments set forth herein. On the contrary, these embodiments are provided to enable a more thorough understanding of the present disclosure and to fully convey the scope of the present disclosure to a person skilled in the art.

An embodiment of the present disclosure provides a recombinant human 2Ig-B7-H3 protein coding gene, in which the gene is:

the nucleotide sequence shown in SEQ ID NO:1.

The recombinant human 2Ig-B7-H3 protein coding gene contains a total of 2765 bases, and a base C located at position 1488 at the 5' end is site-replaced by T.

The present disclosure provides a human 2Ig-B7-H3 protein, the coding gene of the human 2Ig-B7-H3 protein is the recombinant human 2Ig-B7-H3 protein coding gene.

As well known in the art, among the 20 different amino acids that make up the protein, except for Met (ATG) or Trp (TGG) that is encoded by a single codon, the other 18 amino acids are encoded by 2 to 6 codons (Sambrook et al. Molecular Cloning: A Laboratory Manual. $2^{nd}$ Ed., Cold Spring Harbor Laboratory, Cold Spring Harbor Laboratory Press, Cold Spring Harbor, N.Y., 1989, see Appendix D on page 950). That is, due to the degeneracy of the genetic codons, the codons that determine an amino acid are often more than one, the replacement of the third nucleotide in the triplet codon often does not change the composition of the amino acid, so that the nucleotide sequence of the protein encoding the same amino acid sequence can be different. According to the well-known codon table, a person skilled in the art would start from the nucleotide sequence shown in SEQ ID NO:1 disclosed in the present disclosure and obtain the nucleotide sequences by biological methods (such as PCR methods, point mutation methods) or chemical synthesis methods, and apply them into recombination technology and gene therapy, so these nucleotide sequences should be included in the scope of the present disclosure. On the contrary, the use of the DNA sequence disclosed herein can also be carried out by modifying the nucleic acid sequence provided by the present disclosure through methods known in the art, such as the method of Sambrook et al. (Molecular Cloning: A Laboratory Manual. 2nd Ed., Cold Spring Harbor Laboratory, Cold Spring Harbor Laboratory Press, Cold Spring Harbor, N.Y., 1989).

An embodiment of the present disclosure provides a recombinant vector, including a vector and a target gene carried by the vector, in which the target gene is the recombinant human 2Ig-B7-H3 protein coding gene as described in the above technical solutions.

Among them, the target gene may also include regulatory sequences, e.g., a promoter, a terminator and an enhancer for the expression of the one or more target genes. The target gene may also include a marker gene (for example, a gene encoding β-galactosidase, green fluorescent protein, or other fluorescent protein) or a gene whose product regulates the expression of the other genes. In addition to DNA, the target gene can also be mRNA, RNA or rRNA, and can also include related transcriptional regulatory sequences usually associated with transcription sequences, e.g., transcription termination signals, polyadenylation sites, and downstream enhancer elements.

The vector can be various vectors that can carry the target gene commonly used in the art, and various vectors that can carry the target gene available to be improved by technological development. The vectors are, for example, a plasmid (naked DNA), a liposome, a molecular coupler, a polymer, and a viruse.

The plasmid (naked DNA) can carry the target gene, and the plasmid carrying the target gene can be directly injected or introduced into tissue cells through a gene gun, an electroporation and electrofusion technology. In addition, ultrasound helps to improve the efficiency of plasmid transfer. The combination of ultrasound and a microbubble echo contrast agent can increase the permeability of the cell membrane, thereby significantly improving the transfer and expression efficiency of naked DNA. This cell membrane permeation technology can instantly create small holes on the surface of the cell membrane, and then DNA takes the opportunity to enter the cell.

The liposome is a particle composed of lipid bilayers, which can mediate the target gene to pass through the cell membrane. The lipid can be a natural phospholipid, mainly lecithin, derived from egg yolk and soybeans (phosphatidylcholine, PC); it can also be dipalmitoylphosphatidylcholine (DPPC), dipalmitoylphosphatidylethanolamine (DPPE), distearoylphosphatidylcholine (DSPC) and other synthetic phospholipids; and it can also contain cholesterol. The preferred liposomes are cationic liposomes, which are mainly formed by mixing positively charged lipids and neutral auxiliary lipids in an equimolar manner. The positively charged liposomes and the negatively charged DNA can effectively form complexes, which move into cells through endocytosis.

The polymer is a cationic polymer, a cationic polymer, for example, the positive charge on poly-L-lysine is combined with the negative charge on DNA to electrically neutralize guanidine to form a stable polymer/DNA complex. The resulting complex of cationic polymer and DNA is still positively charged, can bind to the negatively charged receptor on the cell surface, and is penetrated into the cell.

The molecular coupling body is to covalently bind the exogenous DNA of the target gene to the ligand of the specific receptor on the cell surface or the monoclonal antibody or the viral membrane protein, and specific binding properties is used to mediate the introduction of exogenous genes into specific types of cells.

Viruses can usually enter specific cells with high efficiency, express their own proteins, and produce new virus particles. Therefore, the engineered virus first becomes a vector for gene therapy. For example, it may be lentiviral vector, retroviral vector, adenovirus vector, adeno-associated virus vector, and herpes simplex virus vector, etc.

The term "expression vector" refers to a vector containing a recombinant polynucleotide, and the recombinant polynucleotide contains an expression control sequence operably linked to the nucleotide sequence to be expressed. Expression vectors include all expression vectors known in the art, including cosmids introduced into recombinant polynucleotides, plasmids (for example, naked or contained in liposomes) and viruses (for example, lentivirus, retrovirus, adenovirus and adeno-associated virus).

The term "lentivirus" belongs to the retroviral family. Lentivirus can infect dividing and non-dividing cells. After lentivirus infection, a large amount of genetic information can be delivered to the host cell, and it can be expressed continuously and stably for a long time, and at the same time it can be inherited stably with cell division. Therefore, lentivirus is one of the most effective tools for introducing foreign genes. Examples of lentivirus include human immunodeficiency virus (HIV), simian immunodeficiency virus (SIV), equine infectious anemia (EIA), and feline immunodeficiency virus (FIV).

Lentiviral vectors can effectively integrate foreign genes into the host chromosome to achieve persistent expression. In terms of infection ability, it can effectively infect neuronal cells, liver cells, cardiomyocytes, tumor cells, endothelial cells, stem cells and other types of cells, so as to achieve good gene therapy effects.

Preferably, the present disclosure uses a lentiviral vector.

The present disclosure also provides a host cell, in which the host contains the recombinant vector of the present disclosure. The recombinant vector containing the recombinant human 2Ig-B7-H3 protein coding gene of the present disclosure is transformed into the host body, which can be used to study the relationship between the expression of tumor cells and the recombinant vector. Preferably, the host is selected from one or more of Escherichia coli, and 239 cells. Among them, Escherichia coli, as a genetically engineered bacteria, can contain the recombinant cloning vector of the present disclosure, thereby realizing the amplification of the recombinant human 2Ig-B7-H3 protein encoding gene of the present disclosure, or it can contain the recombinant expression vector of the present disclosure, thereby realizing the large-scale expression of the recombinant human 2Ig-B7-H3 protein-coding gene of the present disclosure. When the recombinant vector is a recombinant adenovirus vector, the vector can be amplified in 239 cells.

The embodiment of the present disclosure provides a pharmaceutical composition, including excipients and one or more of the human 2Ig-B7-H3 protein and the recombinant vector selected in the above technical solutions.

The pharmaceutically acceptable excipients refer to non-toxic solid, semi-solid or liquid fillers, diluents, encapsulating materials or other formulation excipients, for example, including, but not limited to, saline, buffered saline, glucose, water, glycerol, ethanol and the mixtures thereof. The pharmaceutical composition is suitable for parenteral, sublingual, intracranial, intravaginal, intraperitoneal, intrarectal, intrabuccal or epidermal administration.

Parenteral administration includes intravenous, intramuscular, intraperitoneal, intrasternal, subcutaneous, intraarticular injection and infusion. Pharmaceutical compositions suitable for parenteral administration include sterile aqueous or non-aqueous solutions, dispersions, suspensions or emulsions, and powders for preparation in sterile injectable solutions or dispersions immediately before use. Suitable aqueous or non-aqueous carriers, diluents, solvents or excipients include water, ethanol, glycerin, propylene glycol, polyethylene glycol, carboxymethyl cellulose, vegetable oils and injectable organic esters, such as ethyl oleate. These compositions may also contain preservatives, wetting agents, emulsifiers, protective agents and dispersant adjuvants such as inositol, sorbitol and sucrose. Preferably, osmotic pressure regulators, such as sugars, sodium chloride, and potassium chloride, are added.

Epidermal administration includes administration on the skin, mucous membranes, and on the surface of lung and eyes. Such pharmaceutical compositions include powders, ointments, drops, transdermal patches, iontophoresis devices, inhalants, and the like. The composition for rectal or vaginal administration is preferably a suppository, which can be prepared by mixing the recombinant vector of the present disclosure with a suitable non-irritating excipient (such as cocoa butter, polyethylene glycol or suppository wax). The excipient or carrier is solid at room temperature and liquid at body temperature, so that it melts in the rectum or vagina and releases the active compound.

Preferably, the pharmaceutical composition is an injection, including a pharmaceutically acceptable excipient and one or more selected from the human glucokinase recombinant encoding gene of the present disclosure and the recombinant vector of the present disclosure.

Preferably, the pharmaceutical composition is an injection, including a pharmaceutically acceptable excipient and one or more selected from the recombinant vectors described in the above technical solutions.

The embodiment of the present disclosure provides a use of the recombinant human 2Ig-B7-H3 protein coding gene described in the above technical solutions in the preparation of a medicament for preventing and treating cancer.

After ectopic expression in several mouse tumor cell lines, they can induce tumor-specific cytotoxic T lymphocyte activation, thereby delaying the growth of cancer cells and even completely eliminating tumors. After the transfected cancer cell lines are implanted in mice, they can be significantly prolonged the lifetime of mouse.

The technical solutions of the present disclosure will be further described by way of examples. Those skilled in the art should be understood that these examples are only intended to assist in understanding the present disclosure and are not to be considered as a specific limitation to the present disclosure.

To allow those skilled in the art to understand the features and effects of the present disclosure, the following is merely a general description and definition of terms and wording mentioned in the specification and the scope of patent application. Unless otherwise indicated, all technical and scientific terms used herein have the common meaning to those skilled in the art, and in the case of a conflict, the definition of the specification shall prevail.

Unless otherwise indicated, the experimental methods used in the following examples are conventional methods.

Unless otherwise indicated, the materials, the reagents and the like used in the following examples are commercially available.

Example 1

Human 2Ig-B7-H3 Protein Coding Gene

The recombinant human 2Ig-B7-H3 protein coding gene contains a total of 2765 bases, and a base C located at position 1488 at the 5' end is site-replaced by T.

The nucleotide sequence of the recombinant human 2Ig-B7-H3 protein coding gene is shown in SEQ ID NO:1.

Example 2

Construction of Recombinant Vector

The nucleotide sequence shown in SEQ ID NO: 1 in the sequence listing is inserted between the NEI and NotI restriction sites of pIRES2-EGFP vector, thereby obtaining the recombinant plasmid pIRES2-EGFP/2Ig-B7-H3.

1. LipofectamineTM2000 cationic liposome transfection kit was used and operated according to the kit instructions, and the recombinant plasmid pIRES2-EGFP/2Ig-B7-H3 was introduced into 239T cells to obtain recombinant cells.

2. The recombinant cells obtained in step 1 were inoculated into DMEM/F12 medium containing 5% (volume ratio) newborn calf serum, and then incubated in an incubator at 37° C. and in 5% $CO_2$ for 48 hours, and then the supernatant was collected.

3. The supernatant obtained in step 2 was taken out and filtered with a 0.45 μm filter membrane, and then the filtrate was collected and adjusted the pH to 7.4.

4. The filtrate obtained in step 3 is purified by affinity chromatography.

Equilibrium buffer: 0.5M Tris-HCl buffer with pH 7.4 containing 0.5M NaCl;

Eluent: 0.1M Gly-HCl buffer with pH 3.0.

3 column volumes were first washed with the equilibration buffer, and then the target substance was washed with the eluent at a flow rate of 5 mL/min.

A280 nm detects the UV absorption peak.

A collection tube was used to collect the target peak, and then the solution in the collection tube was transferred to a dialysis bag and dialyzed in 0.01M PBS buffer with pH 7.4 to obtain human 2Ig-B7-H3 protein.

Example 3

Expression of Human 2Ig-B7-H3 Protein Coding Gene on Cell Surface

In order to detect the expression of 2IgB7-H3 on the cell surface, SHG44 and 293T cells were infected with the vector obtained in Example 2 and the negative control lentivirus. The cells were harvested after infection, and the expression of 2IgB7-H3 on the cell surface was detected by flow cytometry.

1. Materials and Instruments
   Target cells: SHG44, 293T.
   Medium: DMEM+10% FBS+1% P/S.
   Flow cytometry reagent: 2IgB7-H3 flow cytometry antibody (human).
   Flow instrument: BD FASAria Cell Sorter.
2. Culture of Cells in Experimental Step 1):
   SHG44 and 293T cells infected with the vector obtained in Example 2 and the negative control lentivirus were cultured in a 37° C. carbon dioxide incubator with 5% $CO_2$.
2) Infection of Cells:
   (1) SHG44 and 293T cells in the logarithmic growth phase were trypsinized to prepare a cell suspension.
   (2) SHG44 and 293T cell suspension were inoculated in a 6-well plate, and cultured overnight in a 37° C. carbon dioxide incubator with 5% $CO_2$.
   (3) An appropriate amount of the vector prepared in Example 2 and the negative control virus were added to each well according to the virus titer, in which the MOI of SHG44 is 100; the MOI of 293T is 2, and the experimental groups are shown as follows:

| 293T | | | |
|---|---|---|---|
| LV-NC | LV-2IgB7-H3-wt− | LV-2IgB7-H3-mu− | LV-2IgB7-H3-wt+ LV-2IgB7-H3-mu |
| SHG44 | | | |
| LV-NC | LV-2IgB7-H3-wt | LV-2IgB7-H3-mu | LV-2IgB7-H3-wt+ LV-2IgB7-H3-mu |

After 48 hours of infection, photographs were taken and recorded.

3) Cell Staining and Detection with Flow Cytometry
   i) To remove the medium, wash twice with PBS, digest the adherent cells on the bottom with trypsin, collect the cells, and centrifuge at 1000 rpm for 5 mins.
   ii) To remove the supernatant, resuspend the cells in 1 ml PBS, and centrifuge them at 1000 rpm for 5 mins.
   iii) To remove the supernatant, resuspend the cells in 500 ul PBS for each sample, and blow them gently.
   iv) To add 2IgB7-H3 flow cytometry antibody and isotype control for each group, and mix them gently.
   v) To incubate for 30 mins at 4° C. in the dark.
   vi) To centrifuge at 1000 rpm for 5 mins, remove the supernatant, and resuspend the cells in 1 ml PBS.
   vii) To centrifuge at 1000 rpm for 5 mins, remove the supernatant, and resuspend the cells in 500 ul PBS.
   viii) To start flow cytometry.

Figure 2:
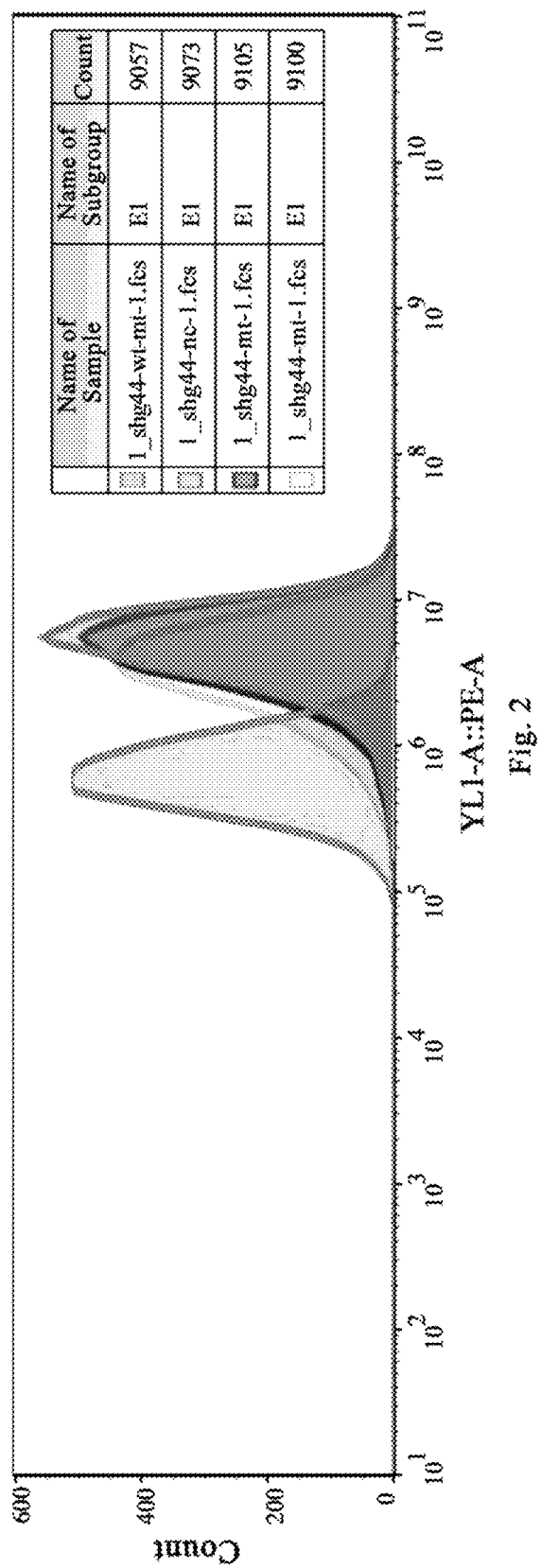
FIG. 2 shows the results of flow cytometric data analysis of SHG44 cells.

4. Experimental Results
Analysis of the Flow Cytometry
The results of flow cytometric data analysis of 293T cells are shown in FIG. 1.
The results of flow cytometric data analysis of SHG44 cells are shown in FIG. 2.

5. Conclusion
As can be seen from the results, the average fluorescence intensity of CD276 in the WT+MT group of antigen-presenting cells 293T and SHG44 cells was higher than those of the WT and MT groups, that is, the expressions of CD276 in the WT and MT groups were higher.

Example 4

Application in Anti-Cancer

The mouse liver cancer H22 cells frozen in liquid nitrogen were quickly thawed in a 37° C. water bath, the cell density was adjusted to $1\times10^7$/mL, and 2 BALB/c mice were intraperitoneally inoculated with 0.2 mL each. After the abdomen of the mouse was swollen, the mouse was sacrificed by cervical dislocation, the abdomen was disinfected, the ascites was extracted and combined, the cell density was adjusted to $1\times10^7$/ml with PBS, and 20 BALB/c mice were subcutaneously inoculated with 0.2 mL each. After 12 days, the mice were divided into two groups, with 10 mice for each group, and the following treatments were carried out:

The first group: no treatment, no vaccination of any therapeutic drugs;

The second group: human 2Ig-B7-H3 protein was injected subcutaneously into the abdomen, immunized 3 times (0.2 mL for each time), and the single immunization dose was 20 ug/mouse;

The first immunization was carried out on the 12th day after the tumor cells were selected: the second immunization was carried out on the 15th day: the third immunization was carried out on the 18th day. From the second day of immunization, the tumor growth was observed, the tumor size was recorded, and the tumor volume was calculated every day according to the following formula: $V=ab^2/2$ (V-volume, a-tumor long diameter, b-tumor short diameter). The changes in tumor volumes were shown in Table 1.

| | Tumor volume on 10 days after tumor inoculation ($mm^3$) | Tumor volume on 13 days after tumor inoculation ($mm^3$) | Tumor volume on 16 days after tumor inoculation ($mm^3$) | Tumor volume on 19 days after tumor inoculation ($mm^3$) |
|---|---|---|---|---|
| Group I | 300 | 500 | 700 | 900 |
| Group II | 300 | 350 | 380 | 400 |

As can be seen from the results, the human 2Ig-B7-H3 protein has a significant therapeutic effect on the subcutaneously inoculated inducible liver cancer model. After treatment with human 2Ig-B7-H3 protein, the growth rate of subcutaneous tumors was significantly slowed down, and the tumor volume became smaller.

Example 5

Human lung adenocarcinoma cells PC-9 were cultured in DMEM medium containing 100 mL/L fetal bovine serum, and transplanted into a round glass-bottom culture dish (Φ=35 mm) at a cell concentration of $1\times10^5$/mL. After culturing at 36° C. in a 5% $CO_2$ cell incubator for 22 hours, the culture solution was discarded and divided into 10 equal parts, and human 2Ig-B7-H3 protein (12 μM, ice bath pre-cooling) dissolved in DMEM medium (hereinafter referred to as "medication") were added; after 2 h incubation in an ice bath and dark, the peptide solution was discarded and washed twice with pre-cooled PBS.

During the operation, the changes in tubulin thickness (i.e., microtubule wall thickness) were observed and recorded. The observation results show that in all 10 experiments, the tubulin thickness of human lung adenocarcinoma cell PC-9 had become thinner. The specific results were shown in Table 2. As can be seen from Table 2, the thickness of tubulin after medication is 80%±2% of that before medication, indicating that the protein of the present disclosure can destroy the microtubule dynamics of cancer cells and acts as an anti-mitotic agent that prevents the proliferation of cancer cells (slow down or prevent the mitosis of cancer cells).

TABLE 2

| | Microtube wall thickness (nm) | |
|---|---|---|
| | Before medication | After 10 weeks of medication |
| Human 2Ig-B7-H3 protein | 5.0 | 4.0 |

Example 6

The experimental subject was a patient with lung adenocarcinoma, clinical stage IV, the synthetic polypeptide was dissolved in PBS (Hyclone) solution with pH 7.4, the concentration was adjusted to 2.5 mg/ml, the upper arm was injected subcutaneously with 200 ug to cover 5% Aldara-cream (iNova Pharmaceuticals Australia Pty Ltd.) for each time, once a week, and 12 weeks as a cycle. ELISA was used to detect the secretion of IFN-γ before medication, and 3 weeks, 7 weeks, and 11 weeks after medication. The synthetic polypeptides used in the specific examples and the test results before and after medication were shown in Table 3.

As can be seen from Table 3, after the medication, the level of IFN-γ secreted by T cells had a significant increase, and even an exponential increase, indicating that the use of the protein of the present disclosure can increase the tumor-killing ability of the peripheral blood of patients with lung adenocarcinoma, and this further confirms the effect of the present disclosure. It was speculated that the protein provided by the present disclosure had obvious curative effect on the treatment of lung adenocarcinoma. Through specific binding with lung adenocarcinoma cells, it induced the cancer cells to produce dendritic cells to form antigen presenting cells, and then to stimulate killer T cells in vivo, thereby realizing the treatment of lung adenocarcinoma.

Subsequently, volunteers without cancer cells in the body was replaced lung adenocarcinoma patients to repeat the above test, and ELISA was used to detect the secretion of IFN-γ before medication, and 3 weeks, 7 weeks, and 11 weeks after medication. It was found that there was no obvious fluctuation, indicating the synthetic polypeptide of the present disclosure has no effect of stimulating the secretion of IFN-γ on a body without cancer cells, and has less toxic and side effects.

TABLE 3

| | IFN-γ concentration (pg/ml) | | | |
|---|---|---|---|---|
| | Before medication | After 5 weeks of medication | After 10 weeks of medication | After 15 weeks of medication |
| Human 2Ig-B7-H3 protein | 18.0 | 50.0 | 210.5 | 680.9 |

The description of the above Examples is merely used for helping to understand the method according to the present disclosure and its core idea. It should be noted that a person skilled in the art may make several further improvements and modifications to the disclosure without departing from the principle of the present disclosure, and these improvements and modifications shall also fall within the scope of the present disclosure.

The above description of the disclosed Examples allows one skilled in the art to implement or use the present disclosure. Various modifications to these Examples would be apparent to one skilled in the art, and the general principles defined herein may be applied to other Examples without departing from the spirit or scope of the disclosure. Therefore, the present disclosure will not be limited to the Examples shown herein, but should conform to the widest scope consistent with the principles and novel features disclosed herein.

What is claimed is:

1. A pharmaceutical composition, comprising a pharmaceutically acceptable excipient and a mixture including both a nucleic acid encoding wild-type 2Ig-B7-H3 protein and a nucleic acid encoding a recombinant human 2Ig-B7-H3 protein, wherein the nucleic acid encoding the recombinant human 2Ig-B7-H3 protein is set forth by SEQ ID NO:1 and the nucleic acid encoding the wild-type 2Ig-B7-H3 protein is set forth by SEQ ID NO:2.

2. The pharmaceutical composition of claim 1, wherein the pharmaceutical composition is an injection solution.

3. A method for treating a liver cancer, comprising administering to a subject in need thereof pharmaceutically acceptable excipient and a mixture including both a nucleic acid encoding wild-type 2Ig-B7-H3 protein and a nucleic acid encoding a recombinant human 2Ig-B7-H3 protein, wherein the nucleic acid encoding is set forth by SEQ ID NO:1 and the nucleic acid encoding the wild-type 2Ig-B7-H3 protein is set forth by SEQ ID NO:2.

4. The pharmaceutical composition of claim 1, wherein the nucleic acid encoding the wild-type 2Ig-B7-H3 protein and the nucleic acid encoding a recombinant human 2Ig-B7-H3 protein are carried by a vector, respectively.

5. The pharmaceutical composition of claim 4, wherein the vector is expressed in a host cell.

6. The pharmaceutical composition of claim 4, wherein the vector is selected from a group consisting of a cloning vector, a eukaryotic expression vector, a prokaryotic expression vector and a shuttle vector.

7. The pharmaceutical composition of claim 4, wherein the vector is selected from a group consisting of a lentiviral vector and an adenoviral vector.

8. The pharmaceutical composition of claim 5, wherein the host cell is selected from one or more of 239T cell and SHG44 cell.

9. The method of claim 3, wherein the nucleic acid encoding the wild-type 2Ig-B7-H3 protein and the nucleic acid encoding a recombinant human 2Ig-B7-H3 protein are carried by a vector, respectively.

10. The method of claim 4, wherein the vector is expressed in a host cell.

11. The method of claim 9, wherein the vector is selected from a group consisting of a cloning vector, a eukaryotic expression vector, a prokaryotic expression vector and a shuttle vector.

12. The method of claim 9, wherein the vector is selected from a group consisting of a lentiviral vector and an adenoviral vector.

13. The method of claim 10, wherein the host cell is selected from one or more of 239T cell and SHG44 cell.

* * * * *